(12) United States Patent
Schally et al.

(10) Patent No.: US 6,184,374 B1
(45) Date of Patent: Feb. 6, 2001

(54) TARGETED CYTOTOXIC ANTHRACYCLINE ANALOGS

(75) Inventors: Andrew V. Schally; Attila A. Nagy; Ren-Zhi Cai, all of Metairie, LA (US)

(73) Assignee: The Administrators of the Tulane Educational Fund, New Orleans, LA (US)

(*) Notice: Under 35 U.S.C. 154(b), the term of this patent shall be extended for 0 days.

(21) Appl. No.: 09/116,125

(22) Filed: Jul. 15, 1998

Related U.S. Application Data

(62) Division of application No. 08/562,652, filed on Nov. 22, 1995, now Pat. No. 5,843,903.

(51) Int. Cl.⁷ ............... C07D 207/00; C07D 207/18; C07D 211/68; C07D 265/00; C12P 17/00
(52) U.S. Cl. ............... 544/63; 530/313; 530/333; 546/1; 546/249; 548/400; 568/591; 568/604
(58) Field of Search ............... 530/313, 333; 544/63; 546/1, 249; 548/400; 568/591, 604

(56) References Cited

U.S. PATENT DOCUMENTS 3,725,350 * 4/1973 Hunsucker et al. ............... 260/67.5

OTHER PUBLICATIONS

Senkus et al. 'Some New Derivatives of Amino Hydroxy Compounds' J. Am. Chem. Soc. vol. 67, pp. 1515–1519, Sep. 1945.*

* cited by examiner

*Primary Examiner*—Michael P. Woodward
*Assistant Examiner*—Anish Gupta

(74) *Attorney, Agent, or Firm*—Omri M. Behr, Esq.

(57) ABSTRACT

This invention is in the field of the chemistry of targeting anticancer anthracycline derivatives. More particularly, it concerns doxorubicin (DOX) or its daunosamine modified derivatives (DM-DOX) linked covalently to analogs of peptide hormones such as LH-RH, bombesin and somatostatin. These covalent conjugates are targeted to various tumors bearing receptors for the peptide hormone analogs. The compounds of this invention are represented by General Formula $Q^{14}$—O—R—P wherein Q has the general formula

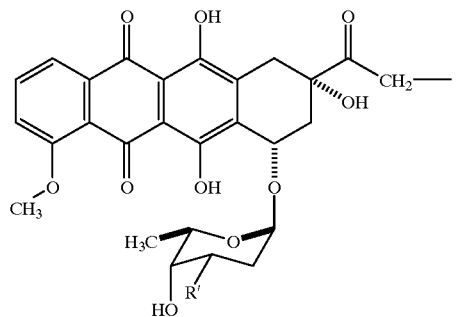

wherein: $Q^{14}$ signifies a Q moiety with a side chain at the 14 position, R— is H or —C(O)—$(CH_2)_n$—C(O)— and n=0–7, R' is $NH_2$ or an aromatic, saturated or partially saturated 5 or 6 membered heterocyclic compounds having at least one ring nitrogen and optionally having a butadiene moiety bonded to adjacent carbon atoms of said ring to form a bicyclic system; P is H or a peptide moiety, suitably an LHRH, somatostatin or bombesin analogs. Nevertheless where R' is $NH_2$ then R and P are other than H. When R and P are H, then R' is other than $NH_2$. A novel synthetic reaction has been discovered in the course of this work to form partially saturated heterocyclic moieties from vicinal and disjunct i.e., α, β or α, γ hydroxy primary amines.

5 Claims, 4 Drawing Sheets

Table 24-2

| No | Group | Mode of administration | | | | | | Final tumor volume (mm³) | Day of measurement | Average survival (days) | Number of surviving mice without tumor from 5 mice per group | |
|---|---|---|---|---|---|---|---|---|---|---|---|---|
| | | Dose/inj. (nmol) | No of injections per week | Pause between injections (days) | Duration of treatment (weeks) | Total amount injected (nmol) | | | | | on day 18 | on day 31 |
| 1 | Control | | | | | | | 7322 | 21 | 22.0±1.6 | 0 | 0 |
| 2 | Q₆ | 1.25 | 2 | 5 | 3 | 7.5 | | 1065 | 16 | 17.4±0.2 † | 0 | 0 |
| 6 | Q₆¹⁴gL | 1.25 | 2 | 5 | 3 | 7.5 | | 863 | 31 | 30.8±0.4 ** | 2 | 0 |
| 3 | Q₆ | 0.5 | 5 | 2 | 3 | 7.5 | | 2531 | 18 | 19.6±0.7 | 0 | 0 |
| 7 | Q₆¹⁴gL | 0.5 | 5 | 2 | 3 | 7.5 | | 3978 | 31 | 26.8±2.6 ** | 1 | 0 |
| 10 | Q₆¹⁴gL | 3.5 | 1 | 6 | 2 | 7 | | 669 | 31 | >31 ** | 4 | 2 |
| 12 | Q₆¹⁴gL | 5.0 | 1 | 6 | 2 | 10 | | 0 | 10 | 13.4 †† | 0 | 0 |
| 13 | DOX | 520 | 1 | 6 | 3 | 1560 | | 784 | 28 | 20 | 1 | 0 |

** Survival is significantly longer (p<0.01) or † (p<0.05) as compared with control data using Duncan's test.
†† Survival is significantly shorter (p<0.01)

FIG. 4

TARGETED CYTOTOXIC ANTHRACYCLINE ANALOGS

This Application is a Divisional of U.S. patent application Ser. No. 08/562,652, filed Nov. 23, 1995, now U.S. Pat. No. 5,843,903.

This invention was made in part with Government support. The Government has certain rights in this application.

BACKGROUND OF THE INVENTION

1. Field of the Invention

This invention is in the field of the chemistry of targeting anticancer anthracycline derivatives. More particularly, it concerns doxorubicin (DOX) or its daunosamine modified derivatives (DM-DOX) linked covalently to analogs of peptide hormones such as LH-RH, bombesin and somatostatin. These covalent conjugates are targeted to various tumors bearing receptors for the peptide hormone analogs.

2. Discussion of the Prior Art

LH-RH Analogs which have cytotoxic moieties at the sixth position are shown in Schally, Janaky and Bajusz, European Patent Publication number 0 450 461 B1, grant publication Sep. 6, 1995.

GnRH (LH-RH) analogs for destroying gonadotrops are described in Nett and Glode, European Patent, international Publication No.: WO 90/09799 published on September 7, 1990.

The patent describes toxins, like ricin, linked to analogs of LH-RH for destroying gonadotrophs and thus curing sex hormone dependent cancers. LH-RH doxorubicin derivative is also mentioned without specification of the chemistry of linking.

Cytotoxic somatostatin analogs are described by Schally et al. in U.S. Patent application filed on Apr. 6, 1990 and refiled in Jul. 15, 1993 under Ser. No. 08/076,846.

A review by A. V. Schally in *Anti-Cancer Drugs* 5, 115–130 (1994) gives details about the presence of receptors on the cell membranes of a wide variety of tumors for analogs of LH-RH, bombesin or somatostatin.

G. Weckbecker lists several references that show the presence of receptors and receptor subtypes for somatostatin analogs on several normal and tumorous tissues in his review in *Farmac. Ther.* 60, 245–264 (1993).

Bombesin-like peptides and the presence of bombesin/GRP receptors for them on various normal and tumorous tissues are discussed in the review by N. Bunnett in *Gut Peptides: Biochemistry and Physiology* 423–445 (1994) Ed.: J. Walsh and G. J. Dockray, Raven Press, New York and by E. Spindell in *Recent Progress in Hormone Research* 48, (1993) (Academic Press).

Doxorubicin is, at this time, the most widely used, and very potent anticancer agent. However, certain tumors do not respond to it at all and its use is also limited by multidrug resistance (MDR) and cardiotoxicity as well as neutropenia, which are the results of chronic treatment. In order to overcome these drawbacks and to further exploit the enormous tumoricidal potential inherent in the structure of anthracycline antibiotics, thousands of synthetic derivatives have been described, including their targeted analogs linked to various carrier macromolecules.

Most of the history of DOX and its analogs is described in "Adriamyc-in", David W. Henry, *ACS Symposium Series*, No. 30, *Cancer Chemotherapy*, American Chemical Society, pp. 15–57 (1976) and in the book Doxorubicin, Federico Arcamone, Academic Press, (1981).

Highly active, alkylating, non-cross resistant 3'-deamino-3'-(3"-cyano-4"-morpholinyl)DOX and derivatives thereof which have antitumor activity are described in Mosher, et al., U.S. Pat. No. 4,464,529, Aug. 7, 1984. The synthesis and biological evaluation of these "Intensely Potent Morpholinyl Anthracyclines" are also described in *J. Med. Chem.* 1984, 27, 638–645.

In *Proc. Natl. Acad. Sci. USA* Vol. 88, pp. 4845–4849, June 1991. Gao et al. describe formaldehyde-mediated alkylation of a DNA sequence by a daunorubicin derivative.

Anthracycline analogues bearing latent alkylating substituents are described in *J. Med. Chem.* 35, 3208–3214 (1992).

The use of an $\alpha$-,$\omega$-diiodo compound for the alkylation of the daunosamine nitrogen of DOX and thus the formation of a new morpholinyl DOX derivative is described in European Patent EP 434 960, filed by Pharmacia Carlo Erba on Dec. 12, 1989.

N-Trifluoroacetyladriamycin$^{14}$-O-hemiglutarate and -hemiadipate are disclosed as analogs of N-trifluoroacetyladriamicyn$^{14}$-O-valerate (AD-32) with improved water solubility in Israel, et al., U.S. Pat. No. 4,299,822, Nov. 10, 1981.

Horton and Priebe (*J. Antibiotics*, XXXVI, 1211–1215.) describe several 14-O-esters of different anthracycline analogs with no dramatic changes in anticancer activity as compared to the 14-OH parent analogs.

In the art of designing targeted chemotherapeutic agents, the following objectives are sought:

1. Stable linkage between the carrier molecule and the chemotherapeutic agent until the target is reached.
2. Retained biological characteristics of the carrier molecule within the conjugate, such as retained binding properties.
3. Retained pharmacological activity of the chemotherapeutic agent within the conjugate, such as retained cytotoxic activity.
4. As a result of conjugation, the production of analogs of more intense activity and/or lower peripheral toxicity relative to the unconjugated moieties.

Conjugation of DOX by $NaIO_4$ oxidation of the daunosamine moiety of DOX followed by reductive alkylation involving a primary amine of a carrier molecule is described in Sela, et al., U.S. Pat. No. 4,263,279, Apr. 21, 1981.

A cis-aconitic acid spacer was used to link the daunosamine nitrogen to macromolecular carriers with a pH-sensitive bond, as described in *Biochem. Biophys. Res. Commun.* 1981 102, 1048–1054.

Morpholino-DOX (a highly active, daunosamine modified analog of DOX) was conjugated to antibody via a hydrolyzable (lysosomotrop, pH sensitive) hydrazone linkage, involving the C-13 oxo function of the cytotoxic agent, as described in *Bioconjugate Chemistry* 1990 1(5), 325–330.

Sensitivity of the carboxamide bond of a leucine residue to enzymatic degradation was used successfully in conjugates of DOX containing a "spacer arm" peptide, preferentially Ala-Leu-Ala-Leu, where the carboxy terminal Leu acylates the daunosamine nitrogen in DOX and the amino terminal Ala is linked to the carrier through dicarboxylic acid spacer as described in *Proc. Natl. Acad. Sci. USA* 1982 79, 626–629.

The daunosamine nitrogen of DOX was acylated by a glutaric acid spacer and linked to LH-RH analogs with a severe loss of cytotoxic activity as described in *Proc. Natl. Acad. Sci. USA* 1992 89, 972–976.

All the citations referred to are incorporated herein by reference.

SUMMARY OF THE INVENTION

The compounds of the invention are novel, targeted cytotoxic peptide hormones comprising an anthracycline cytotoxic agent, such as DOX or DM-DOX, conjugated to a peptide hormone, such as analogs of LH-RH, bombesin, and somatostatin. These cytotoxic peptide hormone conjugates are designed for the treatment of tumors bearing specific receptors for the conjugate, such as breast cancer, ovarian, cancer, endometrial cancer, prostate cancer, pancreatic cancer, colon cancer, gastric cancer, and lung cancer. Certain of these (unconjugated) anthracycline cytotoxic agents utilized herein are per se novel, and are highly potent, their level of toxicity however is too high for them to be used in unconjugated form.

Daunosamine modified DOX analogs presented in this invention were developed during a search for new, highly active, non-cross resistant analogs of DOX suitable for the formation of covalent conjugates with peptide carriers.

The formation of stable, covalently linked conjugates with fully retained biological activities of their components was achieved by using a dicarboxylic acid spacer, like glutaric acid. One carboxyl group of the spacer forms an ester bond with the 14-OH group of DOX or DM-DOX and the other carboxyl group of the spacer forms a carboxamide bond with a well chosen free amino group of the peptide carrier.

The compounds of this invention are represented by General Formula $$Q^{14}\text{—O—R—P} \qquad \qquad I$$

wherein Q has the general formula

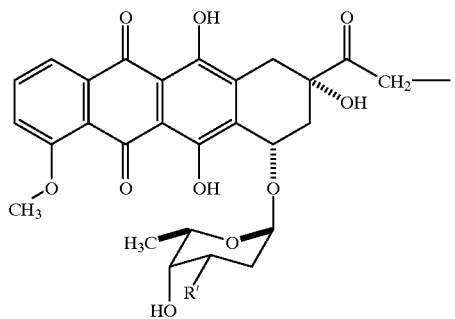

wherein: $Q^{14}$ signifies a Q moiety with a side chain at the 14 position, R— is H or —C(O)—(CH$_2$)$_n$—C(O)— and n=0–7, R' is NH$_2$ or an aromatic, saturated or partially saturated 5 or 6 membered heterocyclic compounds having at least one ring nitrogen and optionally having a butadiene moiety bonded to adjacent carbon atoms of said ring to form a bicyclic system, P is H or a peptide moiety, suitably an LHRH, somatostatin or bombesin analogs, but not excluding other physiologically active peptides. Particularly desirable are those LHRH analogs having affinity for neoplastic cell receptors, especially those analogs having a D-Lys moiety at the 6 position, as well as shortened somatostatin and bombesin analogs. Nevertheless where R' is NH$_2$ then R and P are other than H. When R and P are H, then R' is other than NH$_2$.

A novel synthetic reaction has been discovered in the course of this work. Not only was it found that doxorubicin and its derivatives can be coupled via a dicarboxylic moiety at the 14 position to yield novel pharmacologically effective conjugates but a novel way was provided to form partially saturated heterocyclic moieties from vicinal and disjunct i.e., α, β or α, γ hydroxy primary amines. The particular application in the present invention was the formation of 2"-pyrollinyl and 1",3"-tetrahydropyridinyl moieties on the daunosamine sugar. However, this reaction has broader applicability. 5 and 6 membered partially saturated heterocyclic moieties may be formed when a vicinal or disjunct hydroxy amine is reacted with a halo-substitued aldehyde having 2 or 3 moieties between the aldehyde carbon and the carbon atom having the halo group. These moieties may all be methylene, or a hetero atom such as oxygen may be involved. The reaction takes place in three stages. A very large excess of the haloaldehyde is reacted with the acid salt of the hydroxy amine, suitably in a polar inert anhydrous organic solvent. There is thus formed a five membered oxazolidine ring (or a six-membered 1,3-tetrahydrooxazine ring) by condensation of the aldehyde group with the hydroxyl and the amine groups. This product is treated with a organic base, suitably a tertiary amine, whereby the elements of hydro-halic acid are eliminated between the halo moiety of the former halo aldehyde and the secondary amino group of the oxazolidine or 1,3-tetrahydrooxazine ring to form a fused ring structure by the addition of a 5 or 6 membered ring. The base is then neutralized with a weak acid suitably an organic acid such as glacial acetic acid. Treatment with aqueous acid, suitably an organic acid opens the oxazolidine or 1,3-tetrahydrobxazine portion of the fused ring. It will be understood by those skilled in the art that depending on the starting aldehyde, the final nitrogen contaiing ring may contain at least one additional hetero atom as mentioned above. The general reaction may be illustrated as follows:

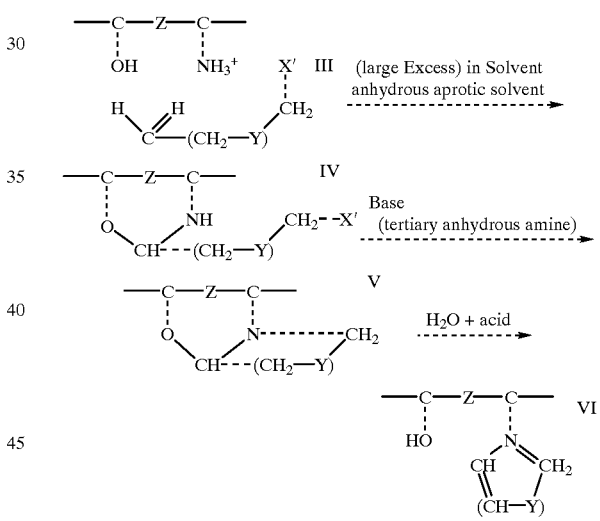

Wherein X' is halo, suitably bromo or iodo, preferably iodo,
Y is CH$_2$, OCH$_2$, CH$_2$–CH$_2$,
Z is nil or CH$_2$ When Z is nil, the aldehyde moiety forms a 5-membered oxazolidine ring as the first step of the reaction. When Z is CH$_2$, the aldehyde moiety forms a 6-membered 1,3-tetrahydrooxazine ring. While such ring formations are well known, in combination with the ring closure effected by the haloalkane side chain in a basic medium such as a tertiary amine in an anhydrous medium, the reaction is new and surprising.

BRIEF DESCRIPTION OF THE DRAWINGS

FIG. 4 is a table (Table 24-2) showing the effect of treatment with cytotoxic LH-RH analog $Q_6^{14}$gL on tumor volumes and survival of mice with estrogen-independent breast cancers.

DESCRIPTION OF THE PREFERRED EMBODIMENTS

Figure 1:
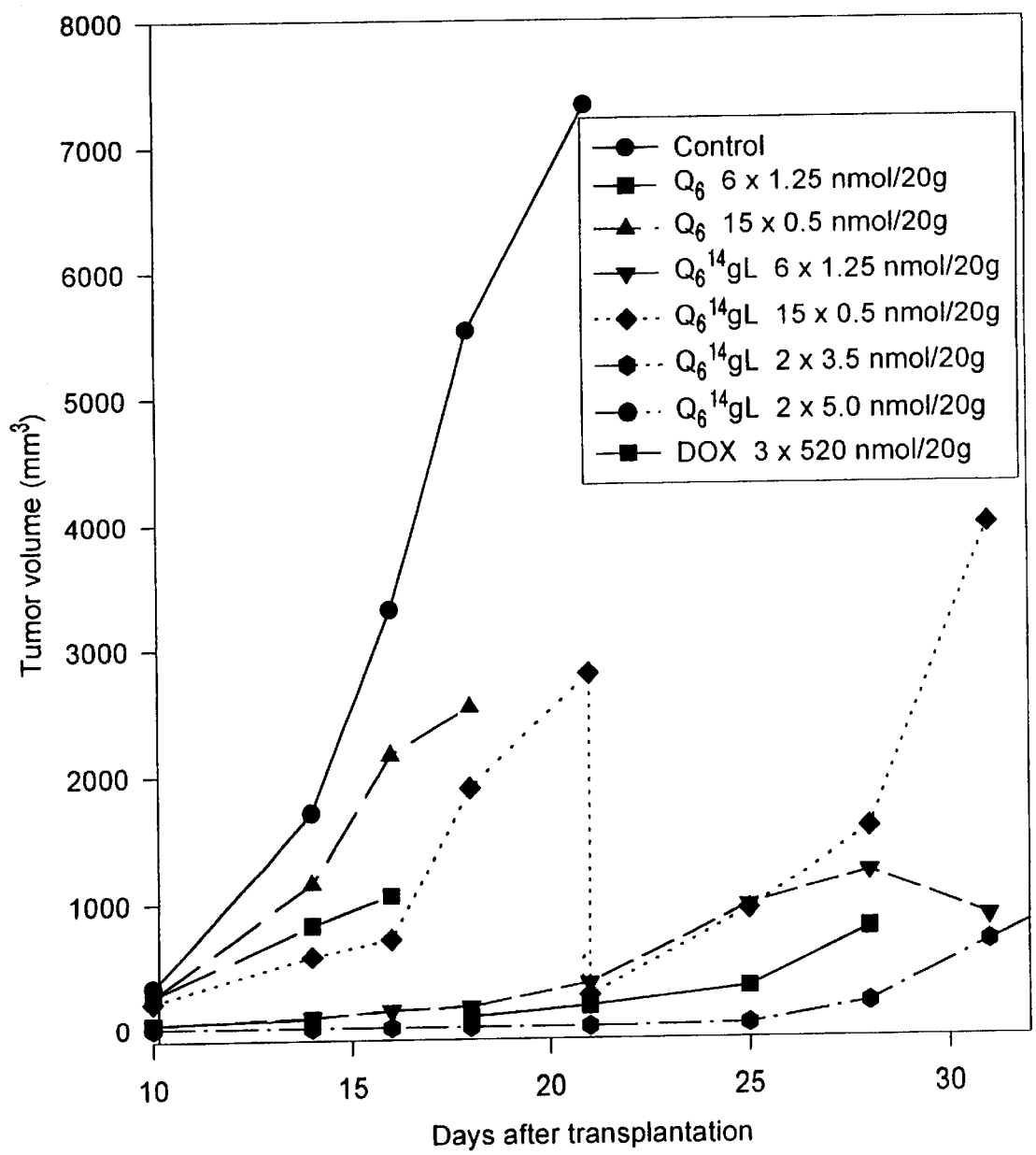
FIG. 1 is plot of volume changes of estrogen independent MXT mouse mammary cancers for different dosage levels of compounds of the present invention and DOX.

The moiety Q, when substituted at R' by certain preferred groups, has submoiety designations of $Q_1$ through $Q_8$, of which $Q_2$ through $Q_8$ are novel cytotoxic moieties.

R' has the preferred values, leading to the desired $Q_x$ moieties listed in parentheses as follows: $NH_2$ ($Q_1$), pyrrolidine-1-yl ($Q_2$), isoindoline-2-yl ($Q_3$), 3-pyrroline-1-yl ($Q_4$), 3-pyrrolidone-1-yl ($Q_5$), 2-pyrroline-1-yl ($Q_6$), 3-piperidone-1-yl ($Q_7$), or 1,3-tetrahydropyridine-1-yl($Q_8$).

Thus if R—P is H and —R' is —$NH_2$, $Q_1$ is DOX, if R—P is H and —R' is pyrrolidine-1-yl, $Q_2$ is 3'-deamino-3'-(pyrrolidine-1"-yl)doxorubicin ($Q_2$); if R—P is H and —R' is isoindoline-2-yl, $Q_3$ is 3'-deamino-3'-(isoindoline-2"-yl) doxorubicin ($Q_3$); if R—P is H and —R' is 3-pyrroline-1-yl, $Q_4$ is 3'-deamino-3'-(3"-pyrroline-1"-yl)doxorubicin ($Q_4$); if R—P is H and —R' is 3-pyrrolidone-1-yl, $Q_5$ is 3'-deamino-3'-(3"-pyrrolidone-1"-yl)doxorubicin ($Q_5$); if R—P is H and —R' is 2-pyrroline-1-yl, $Q_6$ is 3'-deamino-3'-(2"-pyrroline-1"-yl)doxorubicin ($Q_6$); if R—P is H and —R' is 3-piperidone-1-yl, $Q_7$ is 3'-deamino-3'-(3"-piperidone-1"-yl)doxorubicin ($Q_7$); if R—P is H and —R' is 1,3-tetrahydropyridine-1-yl, $Q_8$ is 3'-deamino-3'-(1",3"-tetrahydropyridine-1"-yl)doxorubicin ($Q_8$).

The compounds incorporating the daunosamine nitrogen in a five membered ring with alkylating function are 10–50 times more active in vitro than their homolog counterparts, incorporating the daunosamine nitrogen in a six membered ring. (Such pairs are $Q_5$ and $Q_7$ as well as $Q_6$ and $Q_8$.)

In the preferred embodiments of the present invention, in the subtance of formula $Q^{14}$—O—R—P, R and P are other than hydrogen. Where P is other than hydrogen, that is where it is $P_1$, $P_2$ and $P_3$, suitably where $P_1$ is an LH-RH agonist carrier, an LH-RH antagonist carrier or a shortened LH-RH analog carrier, $P_2$ is a shortened somatostatin analog and $P_3$ is a bombesin antagonist.

Suitably, $P_1$ is Aaa-Bbb-Ccc-Ser-Tyr-D-Lys(Xxx)-Leu-Arg-Pro-Ddd wherein (Xxx) is hydrogen or $A_2$Bu or $A_2$Pr wherein where:

Aaa is Glp, then Bbb is His, Ccc is Trp, and Ddd is Gly-$NH_2$, Aaa is Ac-D-Nal(2), Ac-D-Phe or AcD-Phe(4Cl), then Bbb is D-Phe(4Cl) or D-Phe, Ccc is D-Pal(3) and Ddd is D-Ala-$NH_2$; and where Aaa-Bbb-Ccc is Ac, then Ddd is —NH—$CH_2$—$CH_3$; $P_2$ is Aaa-Cys-Bbb-D-Trp-Lys-Ccc-Cys-Ddd-$NH_2$ wherein where:

Aaa is D-Phe, then Bbb is Tyr, Ccc is Val and Ddd is Thr or Trp; and where Aaa is D-Trp, then Bbb is Phe, and Ccc and Ddd are Thr; and $P_3$ is Aaa-Gln-Trp-Ala-Val-Gly-His-LeuΨBbb-$NH_2$ wherein:

Aaa is nil or D-Phe and Bbb is ($CH_2$—NH)Leu, ($CH_2$—NH)Phe, ($CH_2$—NH)Trp, ($CH_2$—N)Tac or ($CH_2$—N)DMTac.

In the novel compounds of the present invention incorporating analogs of LH-RH, the cytotoxic radical Q is attached to the D-Lys side chain of the LH-RH analogs through a dicarboxylic acid spacer as formulated in Formula VII:

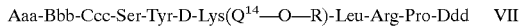

Aaa-Bbb-Ccc-Ser-Tyr-D-Lys($Q^{14}$—O—R)-Leu-Arg-Pro-Ddd     VII

In the novel compounds of the present invention incorporating analogs of somatostatin the cytotoxic radical Q is attached to the amino terminal of the somatostatin analogs through a dicarboxylic acid spacer as formulated in Formula VIII:

VIII

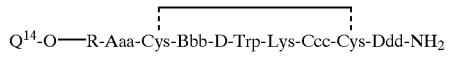

$Q^{14}$-O——R-Aaa-Cys-Bbb-D-Trp-Lys-Ccc-Cys-Ddd-$NH_2$

In the novel compounds of the present invention incorporating analogs of bombesin antagonists, The cytotoxic radical Q is linked to the amino terminal of the bombesin antagonists as formulated in Formula IX:

$Q^{14}$-O-R-Aaa-Gln-Trp-Ala-Val-Gly-His-LeuΨBbb-$NH_2$     IX

Especially preferred embodiments of this invention are those peptide conjugates that contain $Q_1$ and $Q_6$ as the cytotoxic radicals and glutaric acid (n=3) as the dicarboxylic acid spacer forming a 14-O-ester bond with $Q_1$ (doxorubicin) or $Q_6$ (2-pyrrolino-doxorubicin) and a carboxamide bond with the peptide carrier.

The most preferred embodiments of this invention are cytotoxic LH-RH analogs of the following formulae:

1. Glp-His-Trp-Ser-Tyr-D-Lys($Q_1^{14}$-O-glt)-Leu-Arg-Pro-Gly-$NH_2$;
2. Glp-His-Trp-Ser-Tyr-D-Lys($Q_6^{14}$-O-glt)-Leu-Arg-Pro-Gly-$NH_2$; cytotoxic somatostatin analogs of the following formula:

3.

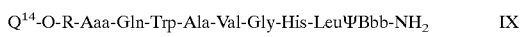

$Q_1^{14}$-O-glt-D-Phe-Cys-Tyr-D-Trp-Lys-Val-Cys-Thr-$NH_2$;

4.

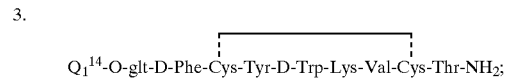

$Q_6^{14}$-O-glt-D-Phe-Cys-Tyr-D-Trp-Lys-Val-Cys-Thr-$NH_2$;

5.

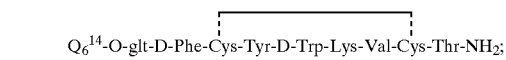

$Q_1^{14}$-O-glt-D-Trp-Cys-Phe-D-Trp-Lys-Val-Cys-Thr-$NH_2$;

6.

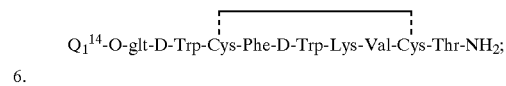

$Q_6^{14}$-O-glt-D-Trp-Cys-Phe-D-Trp-Lys-Val-Cys-Thr-$NH_2$; and cytotoxic bombesin antagonist analogs of the following formula:

7. $Q_1^{14}$-O-glt-Gln-Trp-Ala-Val-Gly-His-LeuΨ($CH_2$—NH)Leu-$NH_2$; and
8. $Q_6^{14}$-O-glt-Gln-Trp-Ala-Val-Gly-His-LeuΨ($CH_2$—NH)Leu-$NH_2$ In the novel process of forming a partially saturated heterocyclic ring with the nitrogen of a vicinal or disjunct i.e., α, β or α, γ hydroxy amine the first step of the reaction is carried out in an anhydrous inert organic polar non-hydroxylic (aprotic) solvent, suitably dimethyl formamide using substantial excess, suitably a 30 fold excess of the halo aldehyde, 4-iodobutyraldehyde and 5-iodovaleraldehyde are especially effective. The invention is not limited to these however, bromo may be used in place of iodo. This reaction as well as the subsequent steps may be carried out at ambient temperature.

The basification step is carried out with an excess, suitably a 2–4 fold excess of an organic base. Tertiary amines such as trialkylalkylamines are suitable for this purpose.

The thus formed bicyclic ring is opened to release the vicinal ot disjunct hydroxyl group by treatment with an organic acid in the presence of water. Dilute aqueous trifuoracetic acid, suitably in an inert organic solvent such as acetonitrile may be used. The product is purified by removal of the volatiles under reduced pressure, excess halo compound extracted with hexane, and the residue purified on HPLC.

Abbreviations

For the description of the peptides and their derivatives of this invention, the conventional abbreviations for the amino acids are used as generally accepted in the peptide chemistry art and as recommended by the IUPAC-IUB Commission on Biochemical Nomenclature (European J. Biochem., 138, 9–37 (1984).

The abbreviations for the individual amino acid residues are based on the trivial name of the amino acid, e.g. Glp is pyroglutamic acid, His is histidine, Trp is tryptophan, etc. The abbreviations indicate the L isomeric form of the amino acids, unless expressed otherwise, e. g., Ser is L-serine, and D-Lys is D-lysine.

Abbreviations of the uncommon amino acids in this invention are as follows: D-Nal(2) is D-3-(2-naphthyl) alanine, and D-Pal(3) is D-3-(3-pyridyl)alanine, D-Phe(4Cl) is D-4-chlorophenylalanine.

Peptide sequences are written according to the convention whereby the N-terminal amino acid is on the left and the C-terminal amino acid is on the right, e.g., Glp-His-Trp.

The formula, LeuΨ($CH_2$—NH)Leu-$NH_2$ describes a reduced peptide bond between a leucine and leucine amide residue at the C-terminal of a peptide sequence.

Other abbreviations used are:
$A_2$Bu: diaminobutyric acid
$A_2$Pr: diaminopropionic acid
BN: bombesin
BOP reagent: benzotriazole-1-yloxitris(dimethylamino) phosphonium hexafluorophosphate
DIPEA: N,N-diisopropylethylamine
DM-DOX: daunosamine modified doxorubicin
DMF: N,N-dimethylformamide
DMTac: 5,5-dimethyl-thiazolidine-4-carboxylic acid
DOX: doxorubicin
Fmoc: 9-fluorenylmithyloxycarbonyl
glt: —C(O)—$CH_2$—$CH_2$—$CH_2$—C(O)-glutaryl
$Glt_2$O: glutaric anhydride
HOBt: 1-hydroxibenzotriazole
HO-glt-OH: glutaric acid
HOSu: N-hydroxysuccinimide
HPLC: high performance liquid chromatography
TFA: trifluoroacetic acid
Tac: thiazolidine-4-carboxylic acid A Beckman analytical HPLC system equipped with model 168 diode array detector and System Gold chromatography software (Beckman) was used to monitor the chemical reactions and to check the purity of the compounds of this invention. The column used was Dynamax C-18 (250×4.6 mm; pore size:300 Å; particle size:12 μm. The solvent system consisted of two components: (i) 0.1% TFA in water, and (ii) 0.1% TFA in 70% aqueous acetonitrile and used in linear gradient mode, growing 1% (ii) in 1 min., for monitoring the chemical reactions. The system was used in isocratic mode for purity control.

A Beckman model 342 semipreparative HPLC system was used for isolation and purification of the compounds of this invention. The column was Aquapore Octyl (250×10 mm; pore size: 300 Å; particle size: 15 μm). The solvent system was the same described for the analytical HPLC above.

Analysis

Figure 2:
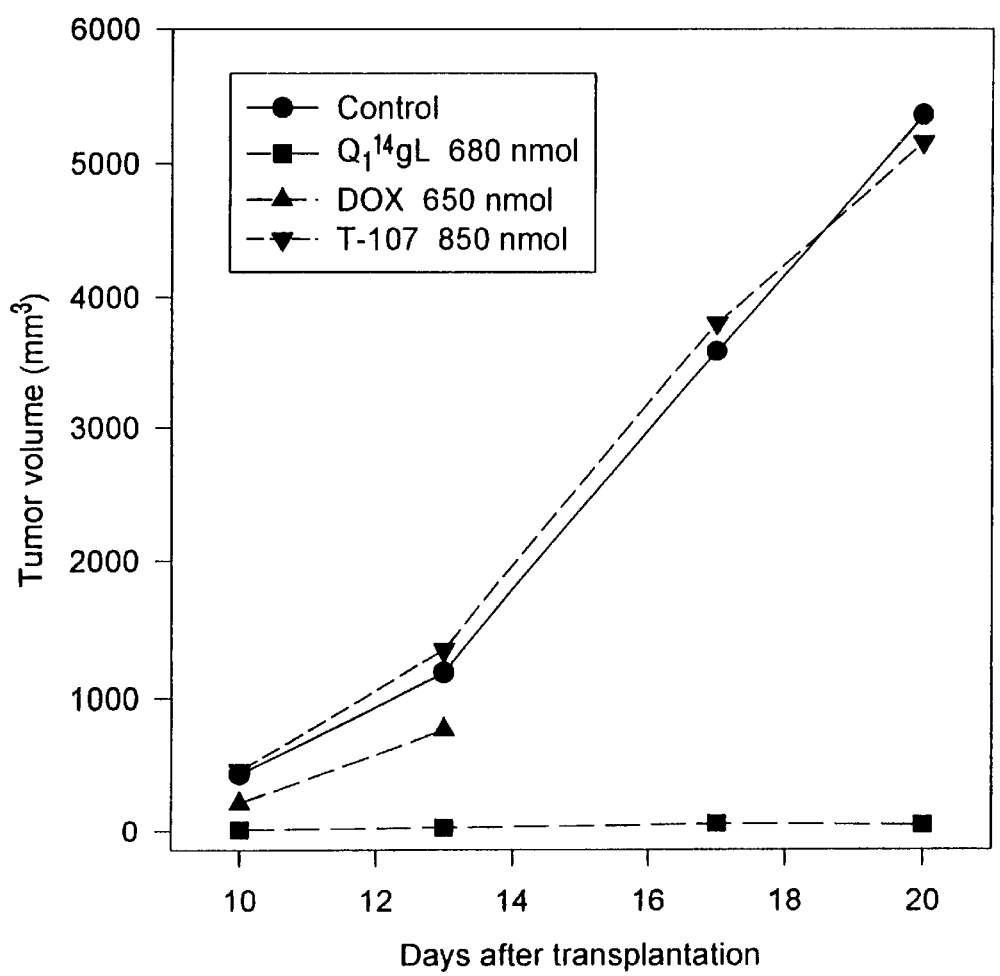
FIG. 2 is plot of volume changes of estrogen independent MXT mouse mammary cancers for different dosage levels of a certain compound of the present invention, a prior art compound, DOX and a control.

Bruker ARX300 NMR spectrometer (300 MHz $^1$H frequency, 75 MHz $^{13}$C frequency) and electrospray mass spectrometer Finnigan-MAT TSQ 7000 were used for the structure identification of the doxorubicin derivatives (FIG. 2).

Synthesis of Peptide Carriers

The peptides of the invention are often administered in the form of pharmaceutically acceptable, nontoxic salts, such as acid additional salts. Illustrative of such acid addition salts are hydrochloride, hydrobromide, sulphate, phosphate, fumarate, glyconate, tannate, maleate, acetate, trifluoroacetate, citrate, benzoate, succinate, alginate, pamoate, malate, ascorbate, tartrate, and the like. If the active ingredient is to be administered in tablet form, the tablet may contain a pharmaceutically acceptable diluent which includes a binder, such as tragacanth, corn starch or gelatin, a disintegrating agent, such as alginic acid and a lubricant, such as magnesium stearate.

If administration in liquid form is desired, sweetening and/or flavoring may be used as part of the pharmaceutically-acceptable diluent, an intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 1 to about 100 micrograms of the peptide per kilogram of the body weight of the host when given intravenously; oral dosages will be much higher. Overall, treatment of subjects with these peptides is generally carried out in the same manner as the clinical treatment using other analogs of LHRH, somatostatin and analogs of doxorubicin.

These peptides can be administered to mammals intravenously, subcutaneously, intramuscularly, orally, intranasally or intravaginally to achieve biological hormonal effects through binding to specific receptors. In the case of LHRH analogs, these effects may include reversible suppression of gonadal activity, and in the case of somatostatin analogs, inhibition or gastrointentinal function. Effective dosages will vary with the form of administration and the particular species of mammal being treated. An example of one typical dosage form is a physiological saline solution containing the peptide which solution is administered to provide a dose in the range of about 0.1 to 2.5 mg/kg of body weight. Oral administration of the peptide may be given in either solid form or liquid form.

The synthesis of the peptide carriers of the present invention can be performed by any techniques that are known to those skilled in the art of peptide chemistry. A summary of the suitable techniques can be found in M. Bodanszky, Principles of Peptide Synthesis, Springer-Verlag, Heidelberg, 1984. Techniques for solid phase peptide synthesis can be found in the textbook of J. M. Stewart and J. D. Young, Solid Phase Peptide Synthesis, Pierce Chem. Co., Rockford, Ill., 1984 (2nd ed.) and in the review of G. Barany et al., *Int. J. Peptide and Protein Res.* 30, 705–739 (1987).

The synthesis of the LH-RH analog carriers used in this invention is detailed in the examples of U.S. Pat. No. 5,258,492, Sandor Bajusz and Andrew V. Schally, Nov. 2, 1993 and in the articles of Bajusz et al., *Proc. Natl. Acad. Sci. USA* 85; 1637–1641 (1988) and 86, 6318–6322 (1989) and Janaky et al., *Proc. Natl. Acad. Sci. USA*, 89, 1023–1027 and 972–976 (1992).

The synthesis of the somatostatin analog carriers used in this invention is detailed in the examples of U.S. Pat. No. 4,650,787, Mar. 17, 1987, Andrew V. Schally and Ren Z. Cai. A description of the synthesis can also be found in the articles by Cai et al., *Proc. Natl. Acad. Sci. USA* 83, 1896–1900 (1986) and *Proc. Natl. Acad. Sci. USA* 84, 2502–2506 (1987).

The synthesis of the bombesin antagonist carriers used in this invention is detailed in the articles by Coy et al., *J. Biol. Chem.* 263, 5056–5060 (1988) and 264, 14691–14697 (1989) and by Cai et al., *Peptides* 13, 267–271 (1992) and *Proc. Natl. Acad. Sci. USA* 91, 12664–12668 (1994).

The synthesis of the doxorubicin derivatives used in this invention and the formation of their conjugates with different peptide carriers is detailed in the following examples which are intended to be illustrative and not limiting:

EXAMPLE 1

Preparation and isolation of N-Fmoc-DOX$^{14}$-O-hemiglutarate

DOX HCl salt, 50 mg(86 $\mu$mol), was dissolved in 1 mL DMF and 30 mg(90 $\mu$mol) Fmoc-OSu was added followed by the addition of 31 $\mu$L (180 $\mu$mol) DIPEA. After stirring for three hours, the reaction was complete as assessed by analytical HPLC. The solvent was evaporated to dryness in Speed Vac high vacuum evaporator and the residue was crystallized by rubbing with 0.1% TFA in H$_2$O. The crystals were filtered and washed once by cold ether to remove traces of excess Fmoc-OSu. After drying in a desiccator, m=62 mg, Yield: 94% 98% pure N-Fmoc-DOX was obtained.

This intermediate was reacted overnight with 11.4 mg(100 $\mu$mol) Glt$_2$O in 1 mL anhydrous DMF in the presence of 26.1 $\mu$L (150 $\mu$mol) DIPEA. The solvent was evaporated in Speed Vac and the residual oil was solidified by rubbing with 0.1% aqueous TFA (v/v). The crude material thus obtained contains 70% N-Fmoc-DOX$^{14}$-O-hemiglutarate, 20% unreacted N-Fmoc-DOX and 10% other impurities as assessed by analytical HPLC. This crude product can be used for the preparation of peptide DOX conjugates without further purification. When this crude material was dissolved in 20 mL 60% aqueous acetonitrile containing 0.1% TFA and applied on semipreparative HPLC, 45.7 mg, 98% pure N-Fmoc-DOX$^{14}$-O-hemiglutarate end product was obtained.

(Yield: 64%.)

EXAMPLE 2

Preparation and isolation of 3'-deamino-3'-(pyrrolidine-1"-yl)doxorubicin TFA salt (Q$_2$) and its 14-O-hemiglutarate (AN-193) TFA salt DOX HCl salt, 50 mg (86 $\mu$mol), was dissolved in 1 mL DMF and 171 $\mu$L (1.3 mmol) 15 fold excess 1,4,-diiodobutane was added followed by the addition of 45 $\mu$L (260 $\mu$mol) 3 fold excess DIPEA. The reaction mixture was stirred overnight at room temperature. After 16 hours the reaction was complete as assessed by analytical HPLC. The solvent is evaporated in Speed Vac and the residual oil is dissolved in 3 mL 0.1% TFA in H$_2$O and extracted with ether to remove excess 1,4-diiodobutane. The aqueous extract was then applied on HPLC and m:41.6 mg, 98% pure DOX derivative was obtained.

(Yield 68%)

The 41.6 mg (58 $\mu$mol) 3'-deamino-3'-(pyrrolidine-1"-yl) doxorubicin TFA salt (Q$_2$) thus obtained was reacted with 1.2 equivalent Glt$_2$O in dry DMF exactly as described in Example 1.

The yield is 35% (16.9 mg) and the purity was 98%.

EXAMPLE 3

Preparation and isolation of 3'-deamino-3'-(isoindoline-2"-yl)doxorubicin TFA salt (Q$_3$)

DOX HCl salt, 50 mg (86 $\mu$mol), was dissolved in 1 mL DMF and 226 mg (1.3 mmol) 15 fold excess $\alpha,\alpha'$-dichloro-ortho-xylene was added followed by the addition of 45 $\mu$L (260 $\mu$mol) 3 fold excess DIPEA and catalytical amount of NaI. After 16 hours the solvents were removed with Speed Vac and the residue was dissolved in 3 mL 0.1% aqueous TFA and extracted with 3 mL ether to remove the excess of the halogen compound. The crude material thus obtained was applied on HPLC. After purification 36 mg, 98% pure end product was obtained.

(Yield: 55%)

EXAMPLE 4

Preparation and isolation of 3'-deamino-3'-(3"-pyrroline-1"-yl)doxorubicin TFA salt (Q$_4$)

DOX HCl salt, 50 mg(86 $\mu$mol), was dissolved in 1 mL DMF and 136.8 $\mu$L (1.3 mmol) 15 fold excess cis-1,4-dichloro-2-butene (Aldrich) was added followed by the addition of 45 $\mu$L (260 $\mu$mol) 3 fold excess DIPEA. After 16 hours the solvents were removed in Speed Vac and the residue was dissolved in 3 mL 0.1% aqueous TFA and extracted with 3 mL hexane to remove the excess of the halogen compound. The crude material thus obtained was applied on HPLC. After purification 22.6 mg, 98% pure end product was obtained.

(Yield:37%)

EXAMPLE 5

Preparation and isolation of 1-chloro-4-bromo-2-butanone (C$_4$H$_6$ClBrO) and 1-chloro-5-bromo-2-pentanone (C$_5$H$_8$ClBrO)

3-Bromopropionyl chloride, 100.8 $\mu$L (1 mmol), (Aldrich), was reacted with excess diazomethane in ether. After 1 hr the ethereal solution was eluted and spot tested on TLC. Thin layer chromatography aluminum sheets pre-coated with silica gel 60 F$_{254}$ by Merck Art No. 5554 was used as the stationary phase and CHCl$_3$:MeOH 95:5 (v/v) as the mobile phase. For the spot test 2,4-dinitrophenylhydrazine reagent (Vogel: A textbook of Practical Organic Chemistry, page 1061, Third Edition, Longmans, N.Y.) was sprayed on the TLC sheet after elution. The diazomethylketone derivative thus formed showed a yellow spot with R$_f$: 0.3. The ethereal solution was then reacted with anhydrous HCl in ether converting the diazomethylketone to the desired end product, 1-chloro-4-bromo-2-butanone. This product showed a yellow spot, characteristic of oxo compounds, with R$_f$: 0.8 in the same solvent system and with the spot test reagent described above. After evaporation of the solvent, the crude product was applied on a column (15 cm long, 2.5 cm in diameter) packed with 15 g silica gel, Merck, grade 9385, 230–400 mesh, pore size 60 Å. The liquid, mobile phase was neat CHCl$_3$. Fractions containing the desired end product (characterized by the spot test detailed above) were mixed and evaporated to dryness. M=1.5 g, clear oil was obtained.

Yield: 80%.

1-chloro-5-bromo-2-pentanone was prepared from 4-bromobutyryl chloride exactly the same way as described for 1-chloro-4-bromo-2-pentanone, except that 4-bromobutyryl chloride was used instead of 3-bromopropionyl chloride. 1.6 g. clear oil was obtained.

Yield: 80%.

EXAMPLE 6

Preparation and isolation of 3'-deamino-3'-(3"-pyrrolidone-1"-yl) doxorubicin TFA salt ($Q_5$)

DOX HCl salt, 50 mg(86 μmol), was dissolved in 1 mL DMF and 241 mg (1.3 mmol) 15 fold excess 1-chloro-4-bromo-2-butanone was added followed by the addition of 45 μL (260 μmol) 3-fold excess DIPEA. After 16 hours the solvents were removed in a Speed Vac and the residue was dissolved in 3 mL 0.1% aqueous TFA and extracted with 3 mL hexane to remove the excess halogen compound. The crude material thus obtained was applied on HPLC. After purification, 20.6 mg, 98% pure end product was obtained.

(Yield: 33%)

EXAMPLE 7

Preparation and isolation of 3'-deamino-3'-(3"-piperidone-1"-yl) doxorubicin TFA salt ($Q_7$)

DOX HCl salt, 50 mg(86 μmol), was dissolved in 1 mL DMF and 260 mg (1.3 mmol) 15 fold excess 1-chloro-5-bromo-2-pentanone was added followed by the addition of 45 μL (260 μmol) 3 fold excess DIPEA. After 16 hours the solvents were removed in a Speed Vac and the residue was dissolved in 3 mL 0.1% aqueous TFA and extracted with 3 mL hexane to remove the excess of the halogen compound. The crude material thus obtained was applied on HPLC. After purification, 18 mg, 95% pure end product was obtained.

(Yield: 28%)

EXAMPLE 8

Preparation and isolation of 4-iodobutyraldehyde and 5-iodovaleraldehyde 2-(3-Chloropropyl)-1,3-dioxolane (4-chloro-n-butyraldehyde ethylene acetal), 1.3 mL (10 mmol), (Fluka) was dissolved in 200 mL acetone containing 30 g (200 mmol, 20-fold excess) NaI. The solution was refluxed for 24 hours followed by evaporation to dryness. 100 mL ether was used to extract the organic material from the inorganic solid residue. The ethereal solution was then washed with 50 mL $H_2O$, 50 mL 5% aqueous $Na_2S_2O_3$ solution and 3 times with 50 mL $H_2O$. The ether was removed in vacuo and the remaining oil was dissolved in 3 mL 50% aqueous acetic acid. After 1 hr 100 mL ether was added to this solution and the acetic acid as well as the ethylene glycol was removed by washing with 50 mL $H_2O$ 3 times. The main product was eluted at $R_f$: 0.8 on TLC in neat $CHCl_3$. The spot test used for the aldehyde function was the same described for the ketones in Example 5. The ether was then removed and the black oil was applied on a column (15 cm long, 2.5 cm in diameter) packed with 15 g silica gel, Merck, grade 9385, 230–400 mesh, pore size 60 Å. The liquid, mobile phase was $CHCl_3$. Fractions containing the desired end product (characterized by the spot test detailed above) were mixed and evaporated to dryness. 1.6 g yellow oil was obtained.

Yield: 80%.

5-Iodovaleraldehyde was obtained exactly the same way starting from 2-(4-chlorobutyl)-1,3-dioxolane (5-chloro-n-valeraldehyde ethylene acetal) (Fluka). 1.65 g yellow oil was obtained.

Yield: 80%.

EXAMPLE 9

Preparation and isolation of 3'-deamino-3'-(2"-pyrroline-1"-yl)doxorubicin TFA salt ($Q_6$)

DOX HCl salt, 50 mg(86 μmol), was dissolved in 1 mL DMF and 515 mg (2.6 mmol) 30-fold excess 4-iodobutyraldehyde was added followed by the addition of 45 μL (260 μmol, 3-fold excess) DIPEA. After 1 hour 100 μL glacial acetic acid was added to the reaction mixture which was then added dropwise to 5 mL of 0.1% TFA in 70% aqueous acetonitrile (solvent ii of the HPLC system). This solution was diluted with 2 mL 0.1% aqueous TFA solution followed by the removal of the acetonitrile in a Speed Vac. The resulting solution was extracted with hexane to remove the excess of the halogen compound. The material thus obtained was applied on HPLC. After purification 52 mg, 98% pure end product was obtained.

(Yield: 85%)

EXAMPLE 10

Preparation and isolation of 3'-deamino-3'-(1",3"-tetrahydropyridine-1"-yl)doxorubicin TFA salt-($Q_8$)

DOX HCl salt, 50 mg(86 μmol), was dissolved in 1 mL DMF and 552 mg (2.6 mmol) 30-fold excess 5-iodovaleraldehyde was added followed by the addition of 45 μL (260 μmol) 3-fold excess DIPEA. After 1 hour 100 μL glacial acetic acid was added to the reaction mixture which was then added dropwise to 5 mL of 0.1% TFA in 70% aqueous acetonitrile (solvent ii of the HPLC system). This solution was diluted with 2 mL 0.1% aqueous TFA solution followed by the removal of the acetonitrile in a Speed Vac. The resulting solution was extracted with hexane to remove the excess halogen compound. The material thus obtained was applied on HPLC. After purification, 46 mg, 98% pure end product was obtained.

(Yield: 75%)

EXAMPLE 11

Preparation and isolation of cytotoxic LH-RH agonist analog containing DOX. ([D-Lys$^6$(DOX$^{14}$-O-glt)]LH-RH, $Q_1^{14}$ gL)

[D-Lys$^6$]LH-RH, 60 mg (37.5 μmol), and 52 mg (64% pure, 37.5 μmol) N-Fmoc-DOX$^{14}$-O-hemiglutarate, (see Example 1), was dissolved in 1 mL DMF and 22 mg (50 μmol) BOP reagent (Aldrich), 13.5 mg (100 μmol) HOBt as well as 52 μL (300 μmol) DIPEA was added. After stirring for 1 hr at room temperature the reaction is complete. The solvents were evaporated and the residual oil was crystallized by 3 mL ethyl acetate and then washed twice with 3 mL ethyl acetate. The 90 mg crude solid material was then dissolved in 3 mL DMF and 300 μL piperidine was added. After 5 minutes, the reaction was placed into an ice bath and was acidified by the addition of a mixture of 300 μL TFA, 700 μL pyridine and 2 mL DMF. After evaporation of the solvents, the residual oil was solidified by ethyl acetate. The crude solid thus obtained, was dissolved in 1 mL 70% aqueous acetonitrile containing 0.1% TFA (i) and diluted with 3 mL 0.1% aqueous TFA (ii) and applied on semi-preparative HPLC. 40 mg (14.8 μmol) 98% pure end product was obtained.

Yield: 48%.

EXAMPLE 12

Preparation of cytotoxic LH-RH agonist analog containing 2-pyrrolino-DOX ([D-Lys$^6$(2-pyrrolino-DOX$^{14}$-O-glt)]LH-RH, $Q_6{}^{14}$gL)

$Q_1{}^{14}$gL, 11.2 mg (5 μmol), (see Example 11) was dissolved in 200 μL DMF and 30 mg (150 μmol, 30-fold excess) 4-iodobutyraldehyde (Example 8) was added followed by the addition of 3 μL (17 μmol) DIPEA. After 1 hour, the reaction was complete (see Example 9) and 10 μL glacial acetic acid was added to the reaction mixture which was then added dropwise to 1 mL 0.1% TFA in 70% aqueous acetonitrile. This solution was then diluted with 1 mL 0.1% aqueous TFA and the acetonitrile was removed in vacuo. The remaining aqueous solution was then extracted with 1 mL hexane and applied on HPLC. m: 7.6 mg, 99% pure end product was obtained.

(Yield: 66%.)

EXAMPLE 13

Preparation and isolation of a cytotoxic somatostatin analog containing DOX

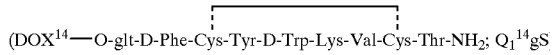

(DOX$^{14}$—O-glt-D-Phe-Cys-Tyr-D-Trp-Lys-Val-Cys-Thr-NH$_2$; $Q_1{}^{14}$gS

D-Phe-Cys-Tyr-D-Trp-Lys(Fmoc)-Val-Cys-Thr-NH$_2$, 20 mg(14.5 μmol) (Proc. Natl. Acad. Sci. USA 1986, pp. 1986–1990.) and 20 mg (64% pure, 14.5 μmol) N-Fmoc-DOX$^{14}$-O-hemiglutarate (Example 1) was dissolved in 200 μL DMF and 8.8 mg (20 μmol) BOP reagent (Aldrich), 5.4 mg (40 μmol) HOBt as well as 17 μL (100 μmol) DIPEA was added. After stirring for 1 hour at room temperature, the reaction was complete. After removal of the solvents in vacuo, the residue was crystallized by ethyl acetate. This solid material was then dissolved in 1 mL DMF and 100 μL piperidine was added. After 7 min the reaction was placed into an ice bath and was acidified by the addition of a mixture of 100 μL TFA, 300 μL pyridine and 2 mL DMF. After evaporation of the solvents, the residual oil was solidified by ethyl acetate. The crude solid thus obtained was dissolved in 1 mL 70% aqueous acetonitrile containing 0.1% TFA (i) and diluted with 3 mL 0.1% aqueous TFA (ii) and applied on semipreparative HPLC. 9.7 mg (5.1 μmol) 95% pure end product was obtained.

Yield: 35%.

EXAMPLE 14

Preparation of cytotoxic somatostatin analog containing 2-pyrrolino-DOX

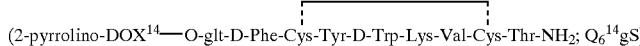

(2-pyrrolino-DOX$^{14}$—O-glt-D-Phe-Cys-Tyr-D-Trp-Lys-Val-Cys-Thr-NH$_2$; $Q_6{}^{14}$gS $Q_1{}^{14}$gS, 9.5 mg (5 μmol), (Example 13) was dissolved in 200 μL DMF and 30 mg (150 μmol) 30-fold excess 4-iodobutyraldehyde (Example 8) was added followed by the addition of 3 μL (17 μmol) DIPEA. After 1 hour, the reaction was complete (Example 9) and 10 μL glacial acetic acid was added to the reaction mixture which was then added dropwise to 1 mL 0.1% TFA in 70% aqueous acetonitrile. This solution was then diluted with 1 mL 0.1% aqueous TFA and the acetonitrile was removed in vacuo. The remaining aqueous solution was then extracted with 1 mL hexane and applied on HPLC. 2.9 mg 95% pure end product was obtained.

(Yield: 30%.)

EXAMPLE 15

Preparation and isolation of a cytotoxic bombesin antagonist containing DOX (DOX$^{14}$-O-glt-Gln-Trp-Ala-Val-Gly-His-LeuΨ(CH$_2$—NH)Leu-NH$_2$, $Q_1{}^{14}$gB)

Gln-Trp-Ala-Val-Gly-His-LeuΨ(CH$_2$—NH)Leu-NH$_2$, 20 mg (15.8 μmol) (Int. J. Peptide Protein Res. 38, 1991, pp. 593–600) and 22 mg (64% pure, 15.8 μmol) N-Fmoc-DOX$^{14}$-O-hemiglutarate (Example 1) was dissolved in 200 μL DMF and 8.8 mg (20 μmol) BOP reagent (Aldrich), 5.4 mg (40 μmol) HOBt as well as 17 μL (100 μmol) DIPEA was added. After stirring for 1 hour at room temperature the reaction was complete. After removal of the solvents in vacuo, the residue was crystallized by ethyl acetate. This solid material was then dissolved in 1 mL DMF and 100 μL piperidine was added. After 5 min the reaction was placed into an ice bath and was acidified by the addition of a mixture of 100 μL TFA, 300 μL pyridine and 2 mL DMF. After evaporation of the solvents, the residual oil was solidified by ethyl acetate. The crude solid thus obtained was dissolved in 1 mL 70% aqueous acetonitrile containing 0.1% TFA (i) and diluted with 3 mL 0.1% aqueous TFA (ii) and applied on semipreparative HPLC. 13.5 mg (7.1 μmol) 98% pure end product was obtained.

Yield: 45%.

EXAMPLE 16

Preparation and isolation of a cytotoxic bombesin antagonistic analog containing 2-pyrrolino-DOX 2-pyrrolino-DOX$^{14}$-O-glt-Gln-Trp-Ala-Val-Gly-His-LeuΨ(CH$_2$—NH)Leu-NH$_2$, $Q_6{}^{14}$gB $Q_1{}^{14}$gB, 9.5 mg (5 μmol), (Example 15) was dissolved in 200 μL DMF and 30 mg (150 μmol, 30-fold excess) 4-iodobutyraldehyde (Example 8) was added followed by the addition of 3 μL (17 μmol) DIPEA. After 1 hour the reaction was complete (Example 9) and 10 μL glacial acetic acid was added to the reaction mixture which was then added dropwise to 1 mL 0.1% TFA in 70% aqueous acetonitrile. This solution was then diluted with 1 mL 0.1% aqueous TFA and the acetonitrile was removed in vacuo. The remaining aqueous solution was then extracted with 1 mL hexane and applied on HPLC. 6 mg 98% pure end product was obtained.

15

(Yield: 60%.)

Determination of in Vitro Cytotoxic Activity

MXT estrogen-independen mouse mammary carcinoma cell line was obtained from Dr. Gunter Berndhart, University of Regensburg, Germany. All the other cell lines used in the determination of the antiproliferative activity of the compounds of this invention were obtained from the American Type Culture Collection (ATCC).

For the evaluation of the activity of the analogs, a colorimetric cytotoxicity assay in microtitration plates was used based on quantification of biomass by staining cells with crystal violet, which correlates very well with determination of cell numbers. (Reile et al.; *Anal. Biochem.* 187, 262–267, 1990; Bernhardt G. et al, *J. Cancer Res. Clin. Oncol.* (1992), 118, 35–43; Spruss Th. et al, *J. Cancer Res. Clin. Oncol* 117, 435–443, 1991; Gillies, R. J., *Anal. Biochem.* 159, 109–113, 1986; Kueng, W. et al.; *Anal. Biochem.*, 182 16–19, 1989.)

Assay Protocol

One to two days after seeding cells in 96-well plates the culture medium is exchanged with fresh medium containing the compounds to be tested and fresh medium only for the control cultures. After varying time of incubation, cells are fixed with glutaric dialdehyde and stored under fetal bovine serum (FBS) at 4° C. until the end of the experiment. Cells are stained with crystal violet and bound stain is extracted with 70% aqueous EtOH. Optical density is measured with EIA Reader (Bio-Tek Instruments) or Biomek 1000 (Beckman) at 590 nm or 600 nm, respectively. Each data point represents the mean value of eight culture wells. T/C values are calculated as $T/C=(T-C_0)/(C-C_0)$ where T=optical density of treated cultures, C=optical density of control (untreated) cultures, $C_0$=optical density of cultures at the start of incubation (t=0).

16

EXAMPLE 17

In vitro cytotoxic activity of daunosamine modified derivatives of DOX

Table 17-1 demonstrates the effects of doxorubicin and its daunosamine modified derivatives on MCF-7 human mammary carcinoma cell line in vitro.

Cytotoxic radicals having their daunosamine N incorporated into a five-membered ring with a reactive functional are 5 to 50 times more active han their homolog counterpart with a six-membered ring as the examples of 3-pyrrolidono-DOX ($Q_5$) and 3-piperidono-DOX ($Q_7$) as well as 2-pyrrolino-DOX ($Q_6$) and 1,3-tetrahydro-pyridino-DOX ($Q_8$) demonstrate.

TABLE 17-1

Effects of Doxorubicin and its Daunosamine modified derivative on MCF-7 Human Mammary Carcinoma CelL Line in vitro
T/C Value at (M)

| Compound | Incubation Time (hr.) | $3 \times 10^{-10}$ | $10^{-9}$ | $3 \times 10^{-9}$ | $10^{-8}$ | $3 \times 10^{-8}$ | $10^{-8}$ |
|---|---|---|---|---|---|---|---|
| Doxorubicin | 70 | | | | 98 | 82 | 54 |
| (DOX) | 120 | | | | 95 | 66 | 33 |
| Pyrrolidino-DOX | 70 | | | | 97 | 25 | −26 |
| ($Q_2$) | 120 | | | | 94 | 17 | −19 |
| Piperidino-DOX | 70 | | | 114 | 70 | 4 | |
| (AN-183) | 120 | | | 109 | 67 | 0 | |
| Isoindolino-DOX | 70 | | | | 118 | 86 | −11 |
| ($Q_3$) | 120 | | | | 108 | 77 | −29 |
| 3-Pyrrolino-DOX | 70 | | | 106 | 72 | | |
| ($Q_4$) | 120 | | | 97 | 65 | −5 | |
| 3-Pyrrolidono- | 70 | | | 87 | 30 | −28 | |
| DOX | 120 | | | 67 | 25 | −10 | |
| ($Q_5$) | | | | | | | |
| 3-Piperidono- | 70 | | | 96 | 80 | 59 | |
| DOX | 120 | | | 97 | 70 | 43 | |
| ($Q_7$) | | | | | | | |
| 2-Pyrrolino-DOX | 70 | 50 | −3 | −18 | | | |
| ($Q_6$) | 120 | 26 | 2 | −9 | | | |
| 1,3-Tetrahydro | 70 | 96 | 88 | 69 | | | |
| pyridino-DOX | 120 | 99 | 93 | 62 | | | |
| ($Q_8$) | | | | | | | |

Cells were incubated in IMEM media containing 5% Hl:DCC-FBS (heat inactivated dextran coated charcoal treated fetal bovine serum) on 96 well plates. Relative cell number in treated and control plates was determined by the crystal violet staining method and was expressed as T/C values where $T/C=T-C_0/C-C_0 \times 100$ [T=absorbance of treated cultures, C= absorbance of control cultures, $C_0$=absorbance of cultures at the start of incubation (t=0). The measured absorbance is proportionate to the cell number.]

Lower T/C values indicate a decrease in the survival of cancerous cells due to treatment. That is to say, 75 would indicate 75% survival of cells as compared to 100% for control or 25% inhibition.

EXAMPLE 18

Full retaining of in vitro cytotoxic activity of DOX in LH-RH agonist peptide conjugate $Q_1{}^{14}gL$ and superactive 2-pyrrolino-DOX ($Q_6$) in LH-RH agonist peptide conjugate $Q_6{}^{14}gL$.

Table 18-1 demonstrates the effects doxorubicin and its daunosamine modified derivative, 2-pyrrolinodoxorubicin ($Q_6$) in comparison with their conjugates with LH-RH agonistic analog, [D-Lys$^6$]LH-RH ($Q_1^{14}$gL and $Q_6^{14}$gL, respectively) on the growth of MCF-7 human mammary carcinoma cell line and MXT estrogen independent mouse mammary carcinoma cell line in vitro.

TABLE 18-1

| Compound | Incubation time (hr) | $3 \times 1^{-11}$ | $10^{-10}$ | $3 \times 10^{-10}$ | $10^{-9}$ | $3 \times 10^{-9}$ | $10^{-8}$ | $3 \times 10^{-8}$ | $10^{-7}$ |
|---|---|---|---|---|---|---|---|---|---|
| | | T/C Value on MCF-7 Cell Line at Conc.(M) | | | | | | | |
| Doxorubicin* | 70 | | | | | | 98 | 82 | 54 |
| | 120 | | | | | | 95 | 66 | 33 |
| $Q_1^{14}$gL | 70 | | | | | | 111 | 89 | 63 |
| | 120 | | | | | | 78 | 55 | 28 |
| $Q_6$ | 70 | | 50 | | −3 | −18 | | | |
| | 120 | | 26 | | 2 | −9 | | | |
| $Q_6^{14}$gL | 70 | | 74 | | 28 | −24 | | | |
| | 120 | | 60 | | 16 | −14 | | | |
| | | T/C value on MXT cell line | | | | | | | |
| Doxorubicin | 26 | | | | | | 85 | 90 | 59 |
| | 50 | | | | | | 74 | 60 | 43 |
| $Q_1^{14}$gL | 26 | | | | | | 87 | 91 | 73 |
| | 50 | | | | | | 71 | 59 | 50 |
| $Q_6$ | 28 | 90 | 78 | 56 | | | | | |
| | 69 | 52 | 6 | −13 | | | | | |
| $Q_6^{14}$gL | 28 | 91 | 78 | 64 | | | | | |
| | 69 | 59 | 15 | −11 | | | | | |

EXAMPLE 19

Table 19-1 demonstrates that the in vitro cytotoxic activity of the somatostatin analogs containing DOX of the invention is fully retained.

Effects of Cytotoxic Analogs of Somatostatin Containing Doxorubicin on the Growth of MIIA PaCa-2 Human Pancreatic Cancer Cell Line in Vitro

| COMPOUND | INCUBATION TIME (h) | T/C VALUE AT CONCENTRATION(M) | | |
|---|---|---|---|---|
| | | $10^{-8}$ | $10^{-7}$ | $10^{-6}$ |
| DOX$^{14}$-O-glt- | 28 | 93 | 95 | 32 |
| S-98* ($Q_1^{14}$gS$^{98}$) | 76 | 103 | 11 | −3 |
| CARRIER | 28 | — | — | 96 |
| ANALOG S-98* | 76 | — | — | 98 |
| DOX$^{14}$-O-glt- | 28 | 93 | 82 | 35 |
| S-121**($Q_1^{14}$gS$^{121}$) | 76 | 97 | 10 | −4 |
| CARRIER | 28 | — | — | 76 |
| ANALOG S-121** | 76 | — | — | 96 |
| DOXORUBICIN | 28 | 95 | 64 | −28 |
| | 76 | 71 | 10 | −7 |

Cells were incubated in RPMI 1640 media containing 10% fetal bovine serum on 96 well plates.

*D-Trp-Cys-Phe-D-Trp-Lys-Thr-Cys-Thr-NH$_2$;

**D-Phe-Cys-Tyr-D-Trp-Lys-Val-Cys-Thr-NH$_2$

EXAMPLE 20

Effects of Cytotoxic Analogs of Bombesin Antagonists Containing Doxorubicin on the Growth of CFPAC-1 Human Pancreatic Cancer Cell In Vitro Table 20-1 demonstrates that the in vitro cytotoxic activity of bombesin antagonistic analogs containing DOX of the invention is fully retained.

TABLE 20-1

| COMPOUND | INCUBATION TIME (h) | T/C VALUE AT CONCENTRATION (M) | | | |
|---|---|---|---|---|---|
| | | $3 \times 10^{-8}$ | $10^{-7}$ | $3 \times 10^{-7}$ | $10^{-6}$ |
| DOX$^{14}$-O-glt- | 66 | 95 | 81 | 44 | 9 |
| B-94 | 95 | 95 | 57 | 28 | 4 |
| ($Q_1^{14}$gB) | 137 | 94 | 28 | 19 | 0 |

TABLE 20-1-continued

| COMPOUND | INCUBATION TIME (h) | T/C VALUE AT CONCENTRATION (M) | | | |
|---|---|---|---|---|---|
| | | $3 \times 10^{-8}$ | $10^{-7}$ | $3 \times 10^{-7}$ | $10^{-6}$ |
| B-94* | 66 | 99 | 106 | 104 | 100 |
| B-94* | 95 | 97 | 99 | 99 | 96 |
| B-94* | 137 | 98 | 98 | 100 | 96 |
| $DOX^{14}$-O-glt-B-50 | 66 | 102 | 78 | 39 | 5 |
| " | 95 | 97 | 55 | 24 | −1 |
| " | 137 | 92 | 28 | 19 | −2 |
| B-50** | 66 | 100 | 93 | 99 | 93 |
| B-50** | 95 | 98 | 100 | 102 | 98 |
| B-50** | 137 | 97 | 98 | 99 | 98 |
| DOX | 66 | 88 | 52 | 15 | −7 |
| " | 95 | 73 | 32 | 10 | −6 |
| " | 137 | 49 | 20 | 7 | −4 |

Preserved Binding Properties of Hormone Derivatives

EXAMPLE 21

Hormonal activities and receptor binding potencies of cytotoxic LH-RH agonist analogs $Q_1^{14}gL$ ([D-Lys$^6$]LH-RH carrying DOX) and $Q_6^{14}gL$ ([D-Lys$^6$] LH-RH carrying 2-Dyrrolino-DOX) in comparison with the carrier peptide, [D-Lys$^6$]LH-RH

TABLE 21-1

| Compounds | Hormonal activity* (LH-responses rel. to LH-RH = 1) | IC$_{50}$** values for rat pituitary receptors (nM) | IC$_{50}$** values for breast cancer receptors (nM) |
|---|---|---|---|
| $Q_1^{14}gL$ | 15 | 2.29 | 7.24 |
| $Q_6^{14}gL$ | 10 | 5.59 | 6.70 |
| [D-Lys$^6$]LH-RH | 8 | 2.26 | 1.80 |

EXAMPLE 22

Somatostatin analogs inhibit the secretion of growth hormone (GH) from perfused rat pituitary as it is described by Carlson et al., Thyrotropin-releasing hormone stimulation and somatostatin inhibition of growth hormone secretion from perfused frat adenohypophyses Endocrinology, 94, 1709–(1974). Accordingly, this method was used to compare the cytotoxic somatostatin analogs of the present invention to their parent carrier molecules with respect to their hormonal activities.

Inhibition of human growth hormone-releasing hormone (hGH-RH(1-29)NH$_2$) induced growth hormone release from superfused rat pituitary cells by somatostatin analogs S-98-l

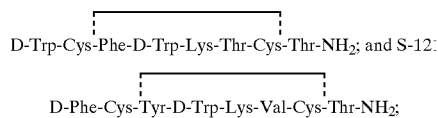

D-Trp-Cys-Phe-D-Trp-Lys-Thr-Cys-Thr-NH$_2$; and S-12:

D-Phe-Cys-Tyr-D-Trp-Lys-Val-Cys-Thr-NH$_2$;

in comparison with their cytotoxic derivative, $Q_1^{14}gS^{98-1}$ ($DOX^{14}$-O-glt-S-98-l) and $Q_1^{14}gS^{121}$ ($DOX^{14}$-O-glt-S-121), respectively.

In rat pituitary superfusion system, the somatostatin analogs were administered for 3 min at 1 nM dose simultaneously with 1 nM hGH-RH(1-29)NH$_2$. The infusion of the somatostatin analogs was maintained for another 6 min. GH responses to 3 min administration of 1 nM hGH-RH(1-29)NH$_2$ were determined during the perfusion of the somatostatin analogs (0 min) and 30, 60 and 90 min after the administration stopped. The data are presented in Table 22-1.

TABLE 22-1

| Somatostatin analogs | GH release** induced by 3 min administration of 1 nM hGH-RH(1–29)NH$_2$ at different time points after infusion of the somatostatin analogs | | | |
|---|---|---|---|---|
| | 0 min | 30 min | 60 min | 90 min |
| S-98-I | 2.9 | 94.7 | 117.6 | — |
| $Q_1^{14}gS^{98}$ | 7.8 | 62.2 | 57.3 | 77.9 |
| S-121 | 0 | 90 | 89.7 | — |
| $Q_1^{14}gS^{121}$ | 8.8 | 58.5 | 54.3 | 67.7 |

**Expressed as percentage of GH release induced by 3 min infusion of 1 nM hGH-RH(1–29)NH$_2$ prior to the administration of the somatostatin analogs.

EXAMPLE 23

Receptor binding studies with cytotoxic bombesin antagonists

Radio iodination of [Tyr$^4$]BN (Sigma) using a Bio-Rad Enzymobead Radio Iodination kit and isolation of mono-iodinated [$^{125}$I-Tyr$^4$]BN was performed as described earlier (1). Binding of labeled [Tyr$^4$]BN and displacement by cytotoxic bombesin antagonist analog, $Q_6^{14}gB$ was conducted using confluent Swiss 3T3 cells (obtained from the American Type Culture Collection) in 24-well plates in a modification (2) of the method of Kris et al (3). Three to five days after seeding, the confluent cells were washed twice with Hanks' Balanced Salt Solution (HBSS) and incubated for 30 min at 37° C. with 50 pM [$^{125}$I-Tyr$^4$]BN in the absence or presence of several concentrations of unlabeled competitors ($Q_6^{14}gB$ or BN) in a total volume of 0.5 ml binding buffer (DMEM with 50 mM HEPES, 0.1% bovine serum albumin (BSA), 5 mM MgCl$_2$ and 100 μg/ml bacitracin, pH: 7.4). Nonspecific binding was determined in the presence of 1 μM unlabeled ligand. After three washings with ice-cold HBSS containing 0.1% BSA (pH: 7.4) the cells were detached with 0.05% Trypsin/0.53 mM EDTA solution and transferred to tubes. Radioactivity was measured with a gamma-counter (Micromedic Systems Inc, Huntsville, Ala.). Binding data were evaluated using radio ligand binding analysis programs by McPherson (4). $K_i$ values presented in Table 23-1, were calculated according to the formula of Cheng and Prusoff (5).

1. Halmos, et al., *Cancer Letters*, 85, 111–118 (1994)
2. Cai, et al., *Proc. Natl. Acad. Sci., USA* 91:12664–12668, (1994.)
3. Kris, et al., *J. Biol. Chem*, 262:11215–11220, (1987.)
4. McPherson, G. A., *J.Pharmaco Methods*, 14:213–228, (1985)
5. Cheng and Prusoff, *Biochem. Pharmacol.* 22:3099–3108, (1973)

Table 23-1

Characterization of the specific binding of cytotoxic bombesin antagonist $Q_6^{14}gB$ (2-pyrrolino-DOX$^{14}$-O-glt-Gln-Trp-Ala-Val-Gly-His-Leu-$\Psi$-(CH$_2$-N)Leu-NH$_2$ to bombesin receptors on Swiss 3T3 cell line in comparison with bombesin

| Compound | $K_i$ (nM) |
|---|---|
| Bombesin | 1.2 |
| $Q_6^{14}gB$ | 1.0 |

Comparative Effectiveness and Toxicity of Hormone Conjugates vs. Cytotoxic Radical Alone intraperitoneally. Groups, treatment schedules and doses as well as average survival times are shown in Table 24-1. Results are summarized in Table 24-2 and FIG. 1.

As is shown in FIG. 4, (Table 24-2), 1.25 nmol $Q_6$ administered on day 1, 2, 7 and 8 (Group 2) exerted strong toxicity characterized with an average survival of 17.4 days, which is significantly shorter than that of the untreated control group. In comparison, the same dosage of $Q_6^{14}gL$ (Group 6) resulted in an average survival of 30.8 days, which is significantly longer than that of the untreated control group. Higher efficacy of $Q_6^{14}gL$ over $Q_6$ can also be demonstrated by comparing the average final tumor volumes in Group 2 (1065 mm$^3$ at day 16) and in Group 6 (863 mm$^3$ at day 31).

Similar conclusions can be demonstrated by comparing $Q_6$ and $Q_6^{14}gL$ in a different treatment schedule where 0.5 nmol of the drugs were administered five days a week for three consecutive weeks.

Doxorubicin at a toxic dose (total amount: 1560 nmol, average survival: 20 days) could not eradicate the tumor, while treatment with $Q_6^{14}gL$ at nontoxic dose (total amount: 7 nmol, average survival: >31 days) to the survival of 2 out of 5 animals, without development of the tumor.

TABLE 24-1

| No of group | Admin. | Dose/ Inj. (nmol) | Dose/ Inj. ($\mu$g) | Inj./ week | Days between Injection | W'ks Admn | Total Amt. Recd | Aver. s'rviv* day |
|---|---|---|---|---|---|---|---|---|
| 1 | Control | | | | | | | 22 |
| 2 | $Q_6$ | 1.25 | 0.92 | 2 | 5 | | | 17.5 |
| 3 | | 0.5 | 0.37 | 5 | 2 | | 7.5 | 19.6 |
| 4 | | 0.25* | 0.19 | | | | 9.5 | 14.6 |
| 5 | | 0.2 | 0.15 | | | | 21 | 13.0 |
| 6 | $Q_6^{14}gL$ | 1.25 | 2.9 | 2 | 5 | 3 | | 30.8 |
| 7 | | 0.5 | 1.16 | 5 | 2 | | 7.5 | 26.8 |
| 8 | | 0.25* | 0.58 | | | | 9.5 | 18.4 |
| 9 | | 0.2 | 0.46 | | | | 21 | 13.6 |
| 10 | | 3.5 | 8.12 | 1 | 6 | 2 | 7 | >31 |
| 11 | | 4 | 9.28 | | | | 8 | |
| 12 | | 5 | 11.6 | | | | 10 | 13.4 |
| 13 | DOX | 520 | 340 | | | 3 | 1560 | 20.0 |

*From day 9 to day 12, dose was raised to 2.5 nmol From day 9 to day 12, dose was raised to 5.0 nmol *Survival

EXAMPLE 24

Treatment with 2-pyrrolino-DOX ($Q_6$), cytotoxic LH-RH agonist analog $Q_6^{14}gL$ ([D-Lys$^6$]LH-RH linked to $Q_6^{14}$-O-hemiglutarate) and (DOX) on estrogen independent MXT mouse mammary cancers (KS-49)

In order to compare the tumor inhibitory activity of cytotoxic doxorubicin derivative, $Q_6$ and its targeted cytotoxic peptide conjugate, $Q_6^{14}gL$ as well as the well known antineoplastic agent, DOX and to determine the optimal way of administration and the nontoxic doses, LH-RH receptor positive MXT (3.2) ovex tumor pieces (1 mm$^3$) were implanted s. c. in female B$_6$D$_2$F1 mice. One day after transplantation the mice were randomly divided into groups of five animals and the treatment started. The compounds were dissolved in 0.1% trifluoroacetic acid (pH 2) and given

EXAMPLE 25

Effects of a single treatment with (DOX), cytotoxic LH-RH analogs T-107 and $Q_1^{14}gL$ on estrogen independent MXT mouse mammary cancers (KS-55)

Test Compounds:

$Q_1^{14}gL$: Doxorubicin $^{14}$-O-hemiglutarate linked to [D-Lys$^6$]LH-RH

T-107: N-glutaryl-doxorubicin linked to [D-Lys$^6$]LH-RH *Proc. Natl. Acad. Sci.* Vol. 89. Pp. 972–976 (1992)); and

DOX

The assays were run as follows:

In order to determine the maximum tolerated doses and compare the effects, MXT (3.2) ovex tumor pieces (1 mm$^3$) were implanted s.c. in female B$_6$D$_2$F1 mice. One day after transplantation the mice were randomly divided into groups of five animals and they were treated with a single injection i.p. The groups and doses are shown in the Table 25-1. The Table also shows the numbers of mice that had tumors when volume was measured and the average survival times for groups. Tumor volume changes are shown in FIG. 2. The compounds were dissolved in 0.1% TFA (pH: 2.0). Tumor volume was measured on days 10, 13, 17, and 20.

As shown in Table 25-1 and FIG. 2, T-107, ([D-Lys$^6$]LH-RH linked to N-glutaryl-DOX) is completely ineffective in inhibiting the growth of this tumor at a dose of 850 nmol/20 g mouse. In contrast, $Q_1^{14}gL$, ([D-Lys$^6$]LH-RH linked to 14-O-glutaryl-DOX) exerted strong suppression of tumor growth (Figure) at a nontoxic dose of 650 nmol/20 g mouse. DOX alone was highly toxic (average survival time: 13.6 days) at a single dose of 650 nmol/20 g mouse and significantly less effective, than $Q_1^{14}gL$ (FIG. 2).

Figure 3:
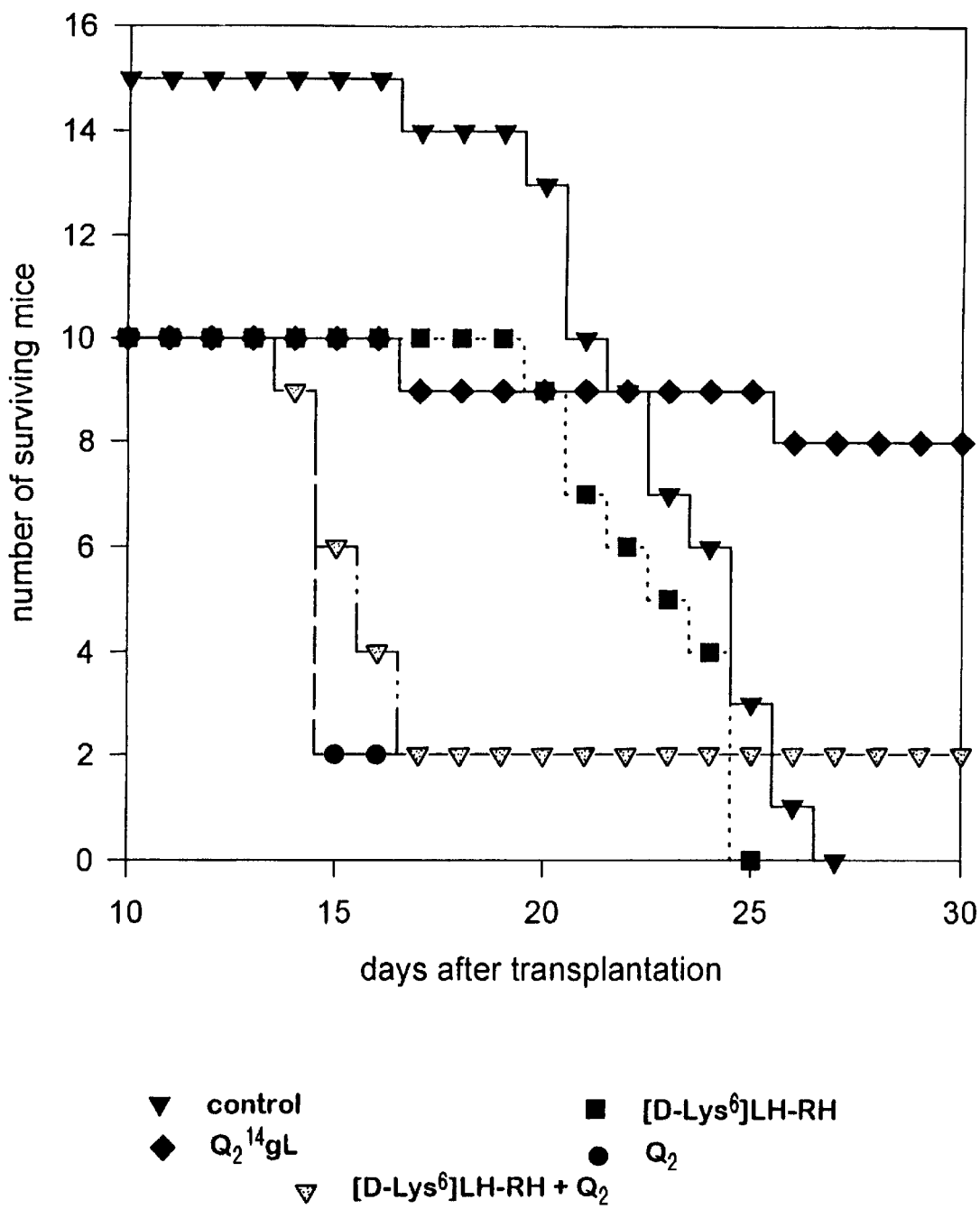
FIG. 3 is plot of the effect of certain cytotoxic LHRH analogs on the survival of mice with estrogen independent MXT mouse mammary cancers.

MXT (3.2) ovex tumor pieces (1 mm$^3$) were transplanted in female $B_6D_2F1$ mice. The treatment started one day after transplantation and was continued for 12 days by i.p. injections once a day. All groups received equimolar amounts of the compounds as shown in Table 26-1. Tumors were measured on days 10, 14 and 18, and tumor volume was calculated. The data are shown in Table 26-1 and in FIG. 3.

Treatment with a daily dose of 30 nmol of daunosamine modified doxorubicin analog $Q_2$ (pyrrolidino-DOX) resulted in strong inhibitory effect on tumor growth (tumor volume: 144 mm$^3$ at day 14 vs. 1391 mm$^3$ for the control group), but exerted severe toxicity killing all the animals before the end

TABLE 25

| No. | Group | Dose | | | Number of tumorous mice/number of surviving mice | | | | Average survival days |
| --- | --- | --- | --- | --- | --- | --- | --- | --- | --- |
| | | nmol/ 20 g | µg/ 20 g | µmol/ kg | Day 10 | Day 13 | Day 17 | Day 20 | |
| 1 | Control | | | | 5/5 | 5/5 | 5/5 | 5/5 | 21.2 ± 0.3 |
| 2 | $Q_1^{14}gL$ | 680 | 1520 | 34 | 1/4 | 2/4 | 2/4 | 3/4 | 28.6 ± 69 35.3 ± 25 ** |
| 3 | $Q_1^{14}gL$ | 710 | 1587 | 35.5 | 2/4 | 3/4 | 3/4 | 3/4 | 26.0 ± 66 32.0 ± 34 * |
| 4 | $Q_1^{14}gL$ | 760 | 1698 | 38 | 3/5 | 4/5 | 4/5 | (Sacr.) | (Sacr.) |
| 5 | DOX | 650 | 427 | 32.5 | 3/3 | 2/2 | 1/1 | 1/1 | 13.6 ± 25 |
| 6 | DOX | 700 | 460 | 35 | 2/3 | 2/3 | 2/2 | | 15.2 ± 24 |
| 7 | DOX | 750 | 493 | 37.5 | 1/1 | | | | 7.8 ± 1.3 |
| 8 | T-107 | 750 | 1676 | 37.5 | 5/5 | 5/5 | 5/5 | 4/4 | 21.8 ± 05 |
| 9 | T-107 | 850 | 1900 | 44.4 | 5/5 | 5/5 | 5/5 | 4/4 | 21.6 ± 07 |

Survival is significantly shorter (p < 0.01) than that of controls
** Survival is significantly longer (p < 0.01) or * (p < 0.05) as compared with control (one mouse which died accidentally on day 2 was left out from these two groups.

EXAMPLE 26

Effect of cytotoxic LH-RH analogs on estrogen independent MXT mouse mammary cancers (KS-47)

Substances Used for Treatment

In an earlier experiment, $Q_2$ at 20 nmol daily dose for 17 days had only a moderate inhibitory effect on tumor growth, and it was toxic at 40 nmol dose (mean survival was 14.6 days). A daily dose of 30 nmol was chosen for the present experiment, which compared the efficacy and toxicity of $Q_2^{14}gL$ ($Q_2$ coupled to [D-Lys$^6$]LH-RH), $Q_2$ (pyrrolidino-doxorubicin), [D-Lys$^6$]LH-RH, and [D-Lys$^6$]LH-RH+$Q_2$.

of the experiment (mean survival 17.9 days). Similarly, $Q_2$ combined (mixture) with [D-Lys$^6$]LH-RH resulted in strong tumor inhibitory effect (tumor volume: 80 mm$^3$ at day 14) but the mean survival (18.5 days) was significantly shorter than that of the untreated control group (23.1 days). As a result of the treatment with $Q_2^{14}gL$, ($Q_2$ covalently linked to [D-Lys$^6$]LH-RH) two animals died, one at day 16 and another at day 26. From the 8 surviving animals only one developed tumors at the last measurement at day 18 and they all looked healthy, but later on all of them started to develop the tumors. The mean survival for this group was significantly longer (28.3 days), than that of the control group. Treatment with [D-Lys$^6$]LH-RH alone did not affect tumor growth.

This experiment demonstrates that the higher efficacy and the lower peripheral toxicity of $Q_2^{14}gL$ over the cytotoxic radical $Q_2$ is attributable to the covalent conjugation of the cytotoxic radical to the targeting carrier LH-RH analog.

TABLE 26-1

Effect of cytotoxic LH-RH analogs on growth of estrogen independent MXT mouse mammary cancers and survival of mice with Tumors

| No | Treatment | Dose ($\mu$g/day) | No. of mice | Mean tumor volume in mm³ on days 10 | 14 | 18 | Mean survival after transplantation (days) |
|---|---|---|---|---|---|---|---|
| 1 | Control | | 15 | 253 | 1391 | 4794 | 23.1 |
| 2 | $Q_2{}^{14}gL$ | 68.7 | 10 | 33 | 16 | 23 | 28.3 * |
| 3 | $Q_2$ | 21.3 | 10 | 153 | 144 | 137 | 17.9 |
| 4 | [D-Lys⁶]LH-RH | 48.0 | 10 | 165 | 1348 | 4003 | 23.5 |
| 5 | [D-Lys⁶]LH-RH + $Q_2$ | 48.0 + 21.3 | 10 | 121 | 80 | 27 | 18.5 |

What is claimed is:

1. A process for the conversion of the nitrogen of a primary amino group of an α, β or α, γ hydroxy primary amino into the nitrogen of a monounsaturated nitrogen containing heterocyclic compound having 5 or 6 atoms in the ring which comprises the sequential steps of
   a) treating said hydroxy amine with an excess of a haloaldehyde, wherein the haloaldehyde has the formula:

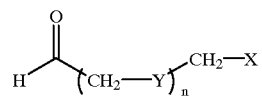

wherein,
n=2 or 3
Y is $CH_2$, $OCH_2$, or $CH_2$—$CH_2$
X is a haloten,
   b) adding and excess, relative to the hydroxamine, of an organic base,
   c) neutralizing the said base with a weak acid, and
   d) treating with a dilute aqueous acid.

2. The process of claim 1 wherein step a) is carried out in an reaction inert aprotic organic solvent.

3. The process of claim 1 wherein step a) is carried out in an reaction inert non hydroxyoic organic solvent.

4. The process of claim 2 wherein the solvent is dimethyl formamide.

5. The process of claim 1 wherein the haloaldehyde is selected from the group consisting of omega bromo- and omega iodo- butyraldehyde and omega bromo- and omega iodo-valeraldehyde.

* * * * *